(12) United States Patent
Leitner et al.

(10) Patent No.: US 8,921,598 B2
(45) Date of Patent: Dec. 30, 2014

(54) METHOD FOR PRODUCING URETHANES COMPOSED OF MONO AND DI-FUNCTIONAL AROMATIC AMINES

(75) Inventors: Andreas Leitner, Pittsburg, PA (US); Robert Baumann, Mannheim (DE); Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 454 days.

(21) Appl. No.: 12/918,617

(22) PCT Filed: Mar. 18, 2009

(86) PCT No.: PCT/EP2009/053169
§ 371 (c)(1),
(2), (4) Date: Aug. 20, 2010

(87) PCT Pub. No.: WO2009/115538
PCT Pub. Date: Sep. 24, 2009

(65) Prior Publication Data
US 2010/0331564 A1    Dec. 30, 2010

(30) Foreign Application Priority Data

Mar. 18, 2008  (EP) .................... 08152939

(51) Int. Cl.
*C07C 231/02*  (2006.01)
*C07C 269/04*  (2006.01)
*C07C 271/28*  (2006.01)

(52) U.S. Cl.
CPC ............. *C07C 269/04* (2013.01); *C07C 271/28* (2013.01)
USPC ....................................... 564/135

(58) Field of Classification Search
USPC .......................................... 548/400; 564/135
See application file for complete search history.

(56) References Cited

U.S. PATENT DOCUMENTS

| | | | |
|---|---|---|---|
| 3,763,217 A | 10/1973 | Brill | |
| 4,268,683 A | 5/1981 | Gurgiolo | |
| 4,268,684 A | 5/1981 | Gurgiolo | |
| 4,395,565 A * | 7/1983 | Romano et al. | 560/24 |
| 4,550,188 A | 10/1985 | Frulla et al. | |
| 5,315,034 A | 5/1994 | Mizia et al. | |

FOREIGN PATENT DOCUMENTS

| | | |
|---|---|---|
| DE | 32 02 690 | 8/1982 |
| EP | 0 048 371 | 3/1982 |
| EP | 0 391 473 | 10/1990 |
| EP | 0 570 071 | 11/1993 |
| WO | 98 55451 | 12/1998 |
| WO | 98 56758 | 12/1998 |
| WO | 2007 015852 | 2/2007 |

OTHER PUBLICATIONS

J. Org. Chem. 2005, 70, 2219-2224, Tundo.*
Pietro Tundo, et al., "Dimethyl Carbonate as an Ambident Electrophile", J. Org. Chem., vol. 70, No. 6, (JOC Article), 2005, pp. 2219-2224.
U.S. Appl. No. 13/008,457, filed Jan. 18, 2011, Bock, et al.
International Search Report issued Aug. 17, 2009 in PCT/EP09/053169 filed Mar. 18, 2009.
U.S. Appl. No. 13/501,621, filed Apr. 12, 2012, Franzke, et al.

* cited by examiner

Primary Examiner — Yong Chu
Assistant Examiner — Sonya Wright
(74) Attorney, Agent, or Firm — Oblon, Spivak, McClelland, Maier & Neustadt, L.L.P.

(57) ABSTRACT

The object of the invention is to provide a process for preparing urethanes by reacting aromatic amines with a dialkyl carbonate, wherein the alkyl radical of the organic dialkyl carbonate comprises from 2 to 18 carbon atoms, and the reaction is carried out in the presence of a base.

20 Claims, No Drawings

METHOD FOR PRODUCING URETHANES COMPOSED OF MONO AND DI-FUNCTIONAL AROMATIC AMINES

The invention provides a process for preparing urethanes by reacting monofunctional and difunctional aromatic amines with a dialkyl carbonate in high yields and selectivities. The urethanes thus prepared can subsequently be converted to industrially relevant isocyanates.

For the preparation of urethanes, a series of processes is known.

In the reactions, for example, Lewis acids, for example uranium salts (U.S. Pat. No. 3,763,217), aluminum turnings with iodine and Hg promoters (U.S. Pat. No. 4,550,188), zinc salts, iron salts, antimony salts and tin salts (U.S. Pat. Nos. 4,268,683, 4,268,684, EP 391473), are used as catalysts. Disadvantages of the industrial use of these processes are the sometimes low conversion, low selectivities or both.

High selectivities and yields are obtained, for example, in Lewis acid-catalyzed processes (Pb salts as catalysts) when a high excess of dialkyl carbonate (amine:carbonate 1:20) is used (WO 98/55451, WO 98/56758). The high excess of dialkyl carbonate leads to large recycle streams.

In other cases, high yields of urethane can be achieved when the urea formed in the urethanization is redissociated thermally to the corresponding urethane in an additional reaction (EP 048371 (catalysts: lead salts, titanium salts, zinc salts and zirconium salts), EP 391473 (catalyst: zinc salts). The redissociation requires an additional, energy-intensive step.

A further disadvantage in the case of use of Lewis acids as homogeneous catalysts is that of the catalyst residues which remain in the product, which can be removed only incompletely.

WO 2007/015852 describes the use of Lewis-acidic heterogeneous catalysts for the urethanization of aromatic amines. This dispenses with a complicated removal of a homogeneous catalyst. The conversions obtained are too low for industrial scale applications and decrease, together with the selectivity, with increasing lifetime of the heterogeneous catalyst.

It is also known that urethanes can be prepared from aromatic amines using basic compounds, for example alkali metal or alkaline earth metal alkoxides.

DE 3202690 describes the preparation of aromatic urethanes by reacting aniline and dialkyl carbonates in the presence of a small amount of a metal alkoxide as a catalyst. The conversions described in the examples are incomplete and the selectivities achieved are insufficient for industrial use.

Journal of Organic Chemistry, 2005, 70, 2219-2224 describes the reaction of aniline with a large excess of dimethyl carbonate (40-fold excess) in the presence of an excess of base such as sodium methoxide (NaOMe) or potassium tert-butoxide (KOtBu). With NaOMe, a selectivity of 67% was obtained after a reaction time of 210 min. With KOtBu, a selectivity of 100% is described after 1 min, which, however, declines to 60% as a result of formation of the N-methylcarbanilate by-product with increasing reaction time. Conversions and isolated yields were not described.

It was an object of the invention to develop a process for preparing urethanes from monofunctional and difunctional aromatic amines, which enables a urethanization reaction in high space-time yields and selectivities with low molar excesses (based on the amino group) of dialkyl carbonate. The urethanes prepared should subsequently be processible to give industrially important aromatic isocyanates.

It has been found that, surprisingly, in contrast to the Journal of Organic Chemistry, 2005, 70, 2219 (see line 15, page 2), by reacting aromatic amines with dialkyl carbonates with alkyl radicals having 2-18, preferably 2-7, carbon atoms, in the presence of stoichiometric amounts of a base, the desired urethane can be isolated in excellent yields (up to 98%) after a short reaction time, even with low excesses of dialkyl carbonate.

The invention provides a process for preparing urethanes by reacting aromatic amines with a dialkyl carbonate, wherein the alkyl radical of the organic dialkyl carbonate comprises from 2 to 18, preferably 2 to 7, carbon atoms, and the reaction is carried out in the presence of a base.

The reaction product of the aromatic amine with the dialkyl carbonate is preferably reacted with a protic compound.

A protic compound is understood to mean a compound which can transfer a proton.

The protic compound is preferably selected from the group comprising alcohols, water and mixtures of the two. Particular preference is given to the use of water.

The base is preferably used in a molar ratio of from 0.8 to 1.2 based on the amino groups.

The dialkyl carbonate is preferably used in a molar ratio of dialkyl carbonate to amino groups of from 1:1 to 10:1, more preferably from 2:1 to 3:1.

The reaction of the aromatic amine with the dialkyl carbonate in the presence of the base is preferably carried out at a reaction temperature of 60-150° C., more preferably at 100-140° C. At this temperature, a quantitative conversion of the aromatic amine to the corresponding urethane can be obtained within 5-60 min. The reaction is typically carried out under standard pressure.

In the process according to the invention, mono- and/or difunctional aromatic amines which preferably do not bear any heteroatoms in the aromatic radical are used. Representatives from this group are, for example, aniline, o-, m-, p-toluidine, o-, m-, p-chloroaniline and isomer mixtures, o-, m-, p-bromoaniline and isomer mixtures, o-, m-, p-trifluoromethylaniline and isomer mixtures, 2,4-, 2,6-, 3,4- and 3,5-dimethyl-, -dichloro-, -dibromo- and -diethylaniline and isomer mixtures, p-t-butylaniline, tolylenediamine (TDA), especially 2,4- and 2,6-tolylenediamine and isomer mixtures thereof, diaminophenylmethane (MDA), especially 2,4'-diaminophenylmethane, 4,4'-diaminophenylmethane, 2,2'-diaminophenylmethane and higher homologs (polyaminopolyphenylmethanes) and isomer mixtures thereof, and m-phenylenediamine.

Preference is giving to using the isomers of tolylenediamine and/or the isomers of diaminophenylmethane.

The alkyl chain of the dialkyl carbonate may be unbranched, branched or cyclic. The alkyl chain is preferably branched or unbranched.

In one embodiment of the invention, the alkyl chain of the dialkyl carbonate is modified with heteroatoms. The heteroatoms may be halogen atoms, preferably fluorine atoms and/or chlorine atoms, more preferably fluorine atoms. In another embodiment, the heteroatoms are oxygen atoms. These are preferably present in the form of ether groups.

In a preferred embodiment of the invention, the dialkyl carbonates are selected from the group comprising diethyl carbonate, di-n-propyl carbonate, di-n-butyl carbonate, di-2-methylpropyl carbonate, di-3-methylbutyl carbonate, di-n-pentyl carbonate, bis-2-methoxyethyl carbonate, bis-2-ethoxyethyl carbonate, bis-2,2,2-trifluoroethyl carbonate, diisobutyl carbonate, preferably diisobutyl carbonate and di-n-butyl carbonate, more preferably diisobutyl carbonate.

The dialkyl carbonate can preferably be prepared by reacting ethylene carbonate with an alcohol.

The base preferably comprises basic organic metal compounds, especially compounds of alkali metals. They may, for example, be compounds comprising nitrogen atoms, for example amides such as sodium amide, or compounds comprising silicon atoms and nitrogen atoms, for example lithium hexamethyldisilazide.

The base more preferably comprises the alkoxides of alkali metals.

The alcohol of the metal alkoxide has 2-18, more preferably 2-7, carbon atoms in the alkyl chain. The alkyl chain may be unbranched, branched or cyclic.

In one embodiment of the invention, the alkyl chain of the corresponding alcohol of the alkoxide is modified with heteroatoms. The heteroatoms may be halogen atoms, preferably fluorine atoms and/or chlorine atoms, more preferably fluorine atoms. In another embodiment, the heteroatoms are oxygen atoms. These are preferably present in the form of ether groups.

In a particularly preferred embodiment of the process according to the invention, the dialkyl carbonates and the metal alkoxides are based on the same alcohol. This has the advantage that, in the process according to the invention, a smaller amount of compounds is present. This reduces the complexity in the process.

The reaction of the aromatic amines with the dialkyl carbonate in the presence of the base is preferably carried out at a reaction temperature of 60-150° C., more preferably at 100-140° C. At this temperature, a quantitative conversion of the aromatic amines can be obtained within 5-60 min. The reaction is typically carried out under standard pressure.

In a preferred embodiment of the process according to the invention for preparing urethanes, in which water is used as the protic compound, the process according to the invention comprises the steps of
a) reacting the aromatic amine with the dialkyl carbonate in the presence of a base
b) reacting the reaction products from step a) with water
c) separating the products formed in step b) and the aqueous base
d) converting the aqueous base from step c) to the corresponding nonaqueous base and recycling it to step a)
e) isolating the urethane removed in step c).

This process can preferably be carried out continuously.

In this process, the urethane is formed in step b).

This embodiment is, in the case of use of water as the protic compound and an alkoxide as the base, shown in FIG. 1.

In this case, the urethane may be isolated as a solution in an organic solvent or as a pure substance in the form of a melt or of a solid.

The products formed in step b) are the urethane and, in the case of use of alkoxides as the base, the alkoxide.

Process step a) is carried out in stage 1 of FIG. 1, process step b) in stage 2. In batchwise mode, stages 1 and 2 can be carried out in the same reaction vessel, and in continuous mode preferably in different reaction vessels.

The product from stage 1) can be transferred into stage 2) without further workup.

In stage 3), the aqueous base obtained in stage 2 is converted to the nonaqueous base, and, in the case of use of metal alkoxides, the hydroxide is converted to the metal alkoxide. This is recycled into stage 1. Excess alcohol which is obtained in stage 2 is discharged there or recycled at another point in the process.

The product from stage 2) is, if it is not already present in this form, separated into an aqueous phase and a nonaqueous phase. This phase is removed from the organic phase which comprises the urethane and isolated as the solid or melt or used directly in this form in further reaction stages, for example in a thermal cleavage to give the corresponding isocyanate. The urethanes removed can, if necessary, be purified, for example by washing.

In a preferred embodiment of the process according to the invention, before step a), the dialkyl carbonate is prepared by reacting ethylene carbonate with an alcohol.

In a further preferred embodiment of the process according to the invention, step e) is followed, as step f), by the cleavage of the urethane to the isocyanate and alcohol. The alcohol formed in step f) can be recycled back into the process. The recycling can, for example, into step d) or into the preparation of the dialkyl carbonates which takes place before step a).

In this invention, it has been shown that the inventive reaction of aromatic amines with a small excess of dialkyl carbonate is possible in high selectivities and high space-time yields. The urethanes are formed in high purities, and so no complicated subsequent purification is required.

The invention will be illustrated in detail in the examples which follow.

EXAMPLE 1

224.0 g (1.3 mol) of diisobutyl carbonate, 39.2 g (0.32 mol) of 2,4-TDA and 64.8 g (0.64 mol) of sodium isobutoxide were weighed successively into a 2 l four-neck flask equipped with stirrer (stirrer speed 200 $min^{-1}$), internal thermometer and argon supply, which was immersed into an oil bath preheated to 120° C. The analysis by thin-layer chromatography after 30 min showed quantitative conversion of the TDA. The flask contents were diluted with 1 l of toluene and 500 ml of water were metered in at 25° C.

After phase separation, the organic phase was washed 3 times with 500 ml of water, the organic phase was subsequently dried over $Na_2SO_4$ and the toluene was concentrated by rotary evaporation. Slightly yellowish crystals (100.1 g) of pure urethane were obtained with a yield of 97%.

EXAMPLE 2

22.4 g (0.13 mol) of diisobutyl carbonate, 3.9 g (0.032 mol) of 2,6-TDA and 6.5 g (0.064 mol) of sodium isobutoxide were weighed successively into a 250 ml four-neck flask equipped with stirrer, internal thermometer and argon supply, which was immersed into an oil bath preheated to 120° C. The analysis by thin-layer chromatography after 30 min showed quantitative conversion of the TDA. The flask contents were diluted with 0.1 l of toluene and 50 ml of water were metered in at 25° C. After phase separation, the organic phase was washed 3 times with 50 ml of water, the organic phase was subsequently dried over $Na_2SO_4$ and the toluene was concentrated by rotary evaporation. Slightly yellowish crystals (9.4 g) of pure urethane were obtained with a yield of 92%.

EXAMPLE 3

224 g (1.30 mol) of diisobutyl carbonate, 39.2 g (0.32 mol) of technical-grade TDA (mixture of 2,4/2,6-TDA=80/20) and 64.8 g (0.64 mol) of sodium isobutoxide were weighed successively into a 250 ml four-neck flask equipped with stirrer, internal thermometer and argon supply, which was immersed into an oil bath preheated to 120° C. The analysis by thin-layer chromatography after 30 min showed quantitative conversion of the TDA. The flask contents were diluted with 1 l of toluene and 500 ml of water were metered in at 25° C. After phase separation, the organic phase was washed 3 times with 500 ml of water, the organic phase was subsequently dried over Na₂SO₄ and the toluene was concentrated by rotary evaporation. Slightly yellowish crystals (102 g) of pure urethane were obtained with a yield of 98%.

EXAMPLE 4

224.0 g (1.3 mol) of di-n-butyl carbonate, 39.2 g (0.32 mol) of 2,4-TDA and 64.8 g (0.64 mol) of sodium n-butoxide were weighed successively into a 2 l four-neck flask equipped with stirrer (stirrer speed 200 min$^{-1}$), internal thermometer and argon supply, which was immersed into an oil bath preheated to 120° C. The analysis by thin-layer chromatography after 30 min showed quantitative conversion of the 2,4-TDA. The flask contents were diluted with 1 l of toluene and 500 ml of water were metered in at 25° C. After phase separation, the organic phase was washed 3 times with 500 ml of water, the organic phase was subsequently dried over Na₂SO₄ and the toluene was concentrated by rotary evaporation. Slightly yellowish crystals (103.1 g) of pure urethane were obtained with a yield of 99%.

EXAMPLE 5

284.1 g (1.3 mol) of diisoamyl carbonate, 39.2 g (0.32 mol) of 2,4-TDA and 74.4 g (0.65 mol) of sodium isoamylate were weighed successively into a 2 l four-neck flask equipped with stirrer (stirrer speed 200 min$^{-1}$), internal thermometer and argon supply, which was immersed into an oil bath preheated to 120° C. The analysis by thin-layer chromatography after 30 min showed quantitative conversion of the TDA. The flask contents were diluted with 1 l of toluene and 100 ml of water were metered in at 25° C. After phase separation, the organic phase was washed 3 times with 100 ml of water, the organic phase was subsequently dried over Na₂SO₄ and the toluene was concentrated by rotary evaporation. Slightly yellowish crystals (106.2 g) of pure urethane were obtained with a yield of 94%.

EXAMPLE 6

125.4 g (0.72 mol) of diisobutyl carbonate, 34.8 g (0.18 mol) of 4,4'-MDA and 36.4 g (0.38 mol) of sodium isobutoxide were weighed successively into a 500 ml four-neck flask equipped with stirrer (stirrer speed 300 min$^{-1}$), internal thermometer and argon line and condenser, which was immersed into an oil bath preheated to 120° C. The analysis by thin-film chromatography after 30 min showed quantitative conversion of the 4,4'-MDA. The flask contents were diluted with 200 ml of toluene and 34.2 g of water were metered in. After stirring for a further 100 min, the mixture was transferred to a 1000 ml separating funnel and the phases were separated. The organic phase was concentrated. Subsequently, the resulting solid was dried fully at 120° C. and 0.25 mbar. Slightly yellowish crystals (61 g) of pure urethane were obtained with a yield of 97%.

The invention claimed is:

1. A process for preparing urethanes by reacting carbocyclic aromatic and/or heteroaromatic amines with a dialkyl carbonate, wherein an alkyl radical of said dialkyl carbonate comprises from 2 to 18 carbon atoms, and the reaction is carried out in the presence of a base comprising
   a) reacting said carbocyclic aromatic and/or heteroaromatic amine with said dialkyl carbonate in the presence of said base
   b) protonating a reaction product from a) with water to form a urethane and an aqueous hydroxide
   c) separating said urethane formed in b) and said aqueous hydroxide
   d) converting said aqueous hydroxide from c) to a corresponding nonaqueous base and recycling it to a)
   e) isolating said urethane removed in c).

2. The process according to claim 1, wherein said base is used in a molar ratio of from 0.8 to 1.2, based on amino groups.

3. The process according to claim 1, wherein said base is a metal alkoxide.

4. The process according to claim 3, wherein an alcohol of said metal alkoxide has 2-18 carbon atoms in a chain.

5. The process according to claim 1, wherein said base is a metal alkoxide of an alcohol having at least one heteroatom interrupting an alkyl chain.

6. The process according to claim 3, wherein alkyl groups of said metal alkoxide are linear or branched.

7. The process according to claim 3, wherein an alcohol of said metal alkoxide is the same as that of said dialkyl carbonate.

8. The process according to claim 1, wherein said carbocyclic aromatic and/or heteroaromatic amine comprises one amino group.

9. The process according to claim 1, wherein said carbocyclic aromatic and/or heteroaromatic amine comprises two amino groups.

10. The process according to claim 1, wherein a carbocyclic aromatic amine is reacted.

11. The process according to claim 1, wherein said carbocyclic aromatic and/or heteroaromatic amine is at least one amine selected from the group consisting of aniline, o-, m-, p-toluidine, o-, m-, p-chloroaniline and isomer mixtures, o-, m-, p-bromoaniline and isomer mixtures, o-, m-, p-trifluoromethylaniline and isomer mixtures, 2,4-, 2,6-, 3,4- and 3,5-dimethyl-, -dichloro-, -dibromo- and -diethylaniline and isomer mixtures, p-t-butylaniline, tolylenediamine, diaminophenylmethane, and higher homologs and m-phenylendiamine.

12. A process for preparing urethanes by reacting carbocyclic aromatic and/or heteroaromatic amines with a dialkyl carbonate and/or a dialkyl carbonate having an alkyl chain interrupted by at least one heteroatom, wherein an alkyl radical of said dialkyl carbonate and/or said dialkyl carbonated having an alkyl chain interrupted by at least one heteroatom comprises from 2 to 18 carbon atoms, and the reaction is carried out in the presence of a base comprising
   a) reacting said carbocyclic aromatic and/or heteroaromatic amine with said dialkyl carbonate and/or dialkyl carbonated having an alkyl chain interrupted by at least one heteroatom in the presence of said base
   b) protonating a reaction product from a) with water to form a urethane and an aqueous hydroxide
   c) separating said urethane formed in b) and said aqueous hydroxide
   d) converting said aqueous hydroxide from c) to a corresponding nonaqueous base and recycling it to a)
   e) isolating said urethane removed in c), wherein said dialkyl carbonate has heteroatoms interrupting an alkyl chain.

13. The process according to claim 1, wherein said dialkyl carbonate is at least one selected from the group consisting of diethyl carbonate, di-n-propyl carbonate, di-n-butyl carbonate, di-2-methylpropyl carbonate, di-3-methylbutyl carbonate and di-n-pentyl carbonate.

14. The process according to claim 1, wherein said dialkyl carbonate is used in a molar ratio of dialkyl carbonate to amino groups of from 1:1 to 10:1.

15. The process according to claim 1, wherein said dialkyl carbonate used in a) is prepared by reacting ethylene carbonate with an alcohol.

16. A process comprising reacting carbocyclic aromatic and/or heteroaromatic amines with a dialkyl carbonate, wherein an alkyl radical of said dialkyl carbonate comprises from 2 to 18 carbon atoms, and the reaction is carried out in the presence of a base comprising
- a) reacting said aromatic and/or heteroaromatic amine with said dialkyl carbonate in the presence of said base
- b) protonating a reaction product from a) with water to form a urethane and an aqueous hydroxide
- c) separating said urethane formed in b) and said aqueous hydroxide
- d) converting said aqueous hydroxide from c) to a corresponding nonaqueous base and recycling it to a)
- e) isolating said urethane removed in c)
- followed by the cleavage f) of said urethane to an isocyanate and alcohol.

17. The process according to claim 1, wherein said aqueous hydroxide formed in b) is reacted with an alcohol to give a corresponding alkoxide which is recycled back into a).

18. The process according to claim 17, wherein water formed in an alkoxide formation is recycled back into b).

19. The process according to claim 11, wherein said higher homolog of diaminophenylmethane is a polyaminopolyphenylmethane.

20. The process according to claim 12, wherein said dialkyl carbonated having an alkyl chain interrupted by at least one heteroatom is at least one selected from the group consisting of bis-2-methoxyethyl carbonate, bis-2-ethoxyethyl carbonate and bis-2,2,2-trifluoroethyl carbonate.

\* \* \* \* \*